United States Patent [19]

Hsieh

[11] Patent Number: 4,608,338

[45] Date of Patent: Aug. 26, 1986

[54] PROCESS FOR BIOCONVERSION-PRODUCT RECOVERY

[75] Inventor: Jih-Han Hsieh, Parsippany, N.J.

[73] Assignee: Celanese Corporation, New York, N.Y.

[21] Appl. No.: 387,083

[22] Filed: Jun. 10, 1982

[51] Int. Cl.$^4$ .......................... C12P 7/44; C12P 17/04; C12P 7/50; C12R 1/40
[52] U.S. Cl. ................................... 435/142; 435/126; 435/143; 435/190; 435/803; 435/877
[58] Field of Search ............... 435/136, 142, 189, 190, 435/253, 877, 813, 803, 126

[56] References Cited

U.S. PATENT DOCUMENTS 3,729,378  6/1970  Imai et al. ............................ 435/136
4,167,450  9/1979  Chesbro et al. ...................... 435/289
4,355,107 10/1982  Maxwell .............................. 435/253

OTHER PUBLICATIONS

*Dictionary of Organic Compounds,* vol. 2, Oxford University Press, N.Y. (1936), p. 841.

*Primary Examiner*—Thomas G. Wiseman
*Attorney, Agent, or Firm*—Depaoli & O'Brien

[57] ABSTRACT

This invention provides an improved bioconversion system in which a non-growth organic substrate is biooxidized to a carboxylic acid product, and the carboxylic acid product is recovered as a precipitate and the resultant fermentation broth is suitable for recycle to the bioreactor. A useful water-insoluble salt is also recovered as a byproduct of the process.

14 Claims, No Drawings

PROCESS FOR BIOCONVERSION-PRODUCT RECOVERY

BACKGROUND OF THE INVENTION

Carboxylic acids are important high volume commodities in the chemical industry. For example, it is estimated that the 1982 worldwide capacity for adipic acid is about five billion pounds.

Adipic acid is produced by oxidation of cyclohexane or cyclohexanol with nitric acid in the presence of a vanadium-copper catalyst. Other methods of synthesizing adipic acid include 1,3-butadiene carbonylation with carbon monoxide followed by hydrolysis; methyl acrylate dimerization; and 1,4-butanediol carbonylation.

The surge of recent biotechnical advances has increased interest in the potential application of bioconversion systems for the production of high volume chemicals such as adipic acid and other carboxylic acids and commercially established commodities.

One prospective new method of synthesizing a carboxylic acid such as adipic acid is by the hydrogenation of muconic acid, which is a diolefinically unsaturated adipic acid derivative:

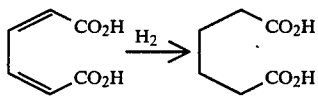

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27 469–546(1965) by Interscience Publishers.

The Journal of Biological Chemistry, 241(16), 3776 (1966) reports the conversion of catechol and protocatechuate to $\beta$-ketoadipate by *Pseudomonas putida*. The conversion of catechol proceeds by the ortho pathway via a muconic acid intermediate:

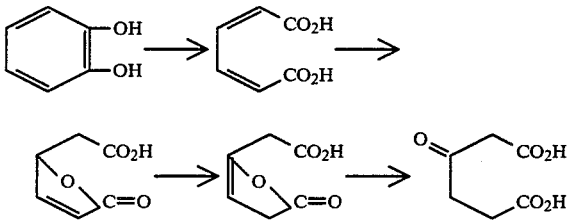

The chemical structures illustrated in the reaction scheme are catechol, muconic acid, muconolactone, $\beta$-ketoadipate enollactone and $\beta$-ketodipate, respectively.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through $\beta$-ketoadipate to a biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed $\beta$-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an aromatic hydrocarbon substrate such as toluene by the ortho pathway via muconic acid and $\beta$-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation.

The said construction of the desirable mutant strains recently has been achieved, as exemplified by *Pseudomonas putida* Biotype A strain ATCC No. 31,916.

As a consequence of the prospect of large scale bioconversion systems for production of carboxylic acid type compounds from lower cost hydrocarbon substrates, the problems of efficient recovery of bioconversion products contained as low concentration solutes in fermentation culture media are of increasing significance. Further, an ancillary concern relates to the storage or disposal of prospective waste streams which are generated by the bioconversion systems.

Accordingly, it is an object of this invention to provide improved methods for the recovery of metabolic products from bioconversion systems.

It is another object of this invention to provide a process for the separation and recovery of carboxylic acids which are contained as bioconversion products in aqueous fermentation culture media.

It is a further object of this invention to provide an improved process for the recovery of extracellular muconic acid product from an aqueous fermentation medium in which a toluene substrate is bio-oxidized, and which process yields a recoverable cell-free fermentation broth which can be recycled in the bioconversion system.

Other objects and advantages will become apparent from the accompanying description and examples.

DESCRIPTION OF THE INVENTION

One or more objects of the present invention are accomplished by the provision of an improvement in a microbial bioconversion process in which a non-growth organic substrate in an aqueous fermentation medium is bio-oxidized by whole cells to an extracellular carboxylic acid product having a solubility of less than about 1.0 weight percent in the aqueous fermentation medium, the improvement which comprises maintaining approximately neutral pH conditions in the fermentation medium by the addition of ammonia during the bioconversion period, separating the microbial cells from the fermentation medium to provide a cell-free fermentation broth containing ammonium carboxylate product, adding sulfuric acid or phosphoric acid to the fermentation broth to precipitate the carboxylate product in the free carboxylate acid form, separating the carboxylic acid precipitate from the fermentation broth and treating the fermentation broth with a basic reagent selected from metal hydroxides, oxides and carbonate compounds which causes the precipitation of a water-insoluble metal salt, and separating the metal salt precipitate to provide a resultant fermentation broth for recycle which contains a water-soluble ammonium compound.

The invention process generally is applicable for the recovery of any carboxylic acid metabolite which accumulates as an extracellular product, and which carboxylic acid in the free acid form has a solubility of less than about 1.0 weight percent in an aqueous fermentation medium under ambient conditions, e.g., at about 20°-30° C., and at a fermentation medium pH of less than about 3.0.

Illustrative of carboxylic acid metabolites which can be separated and recovered from fermentation media include aliphatic and aromatic carboxylic acids such as pyruvic acid, butanoic acid, hexanoic acid, succinic acid, glutaric acid, ketoadipic acid, muconic acid, $\alpha,\alpha$-dimethylmuconic acid, $\beta$-carboxymuconic acid, benzoic acid, alkylbenzoic acid, salicylic acid, phenylacetic acid, phenylpyruvic acid, nicotinic acid, and the like.

The addition of the sulfuric acid or phosphoric acid to the cell-free fermentation medium as described above converts ammonium carboxylate to its free carboxylic acid form. Under the acidic conditions (e.g., a pH of less than about 3) the carboxylic acid product precipitates out of solution. It is readily separated from the aqueous fermentation medium by filtration or other conventional means.

The acidic aqueous fermentation broth which remains after removal of the carboxylic acid precipitate is then neutralized with a basic reagent selected from metal hydroxides, metal oxides and metal carbonates which interact with water-soluble ammonium sulfate or ammonium phosphate to form a water-insoluble sulfate or phosphate salt.

Illustrative of suitable basic reagents are the hydroxides, oxides and carbonates of metals such as magnesium, calcium, zinc and barium. Calcium carbonate is the preferred basic reagent.

After the removal of the water-insoluble metal salt precipitate from the treated fermentation broth, the resultant fermentation broth is suitable for recycle to the fermentor. The recycle fermentation broth contains a water-soluble ammonium compound, such as ammonium hydroxide or ammonium carbonate.

Because of the presence of the ammonium compound in the recycle fermentation broth, the quantity of ammonia added to the bioconversion zone as previously described can be reduced in an amount corresponding to the ammonium compound molar content in the recycle fermentation broth.

The recycle fermentation broth is usually sterilized before it is introduced into the fermentor. In the case of a continuous bioconversion system, the said fermentation broth is recycled continuously.

Illustrative of a particular embodiment, the present invention provides an improved microbial bioconversion process in which a toluene substrate in an aqueous fermentation medium is bio-oxidized by whole cells to an extracellular muconic acid product, the improvement which comprises maintaining approximately neutral pH conditions in the fermentation medium by the addition of ammonia during the bioconversion period, separating the microbial cells from the fermentation medium to provide a cell-free fermentation broth containing ammonium muconate product, adding sulfuric acid or phosphoric acid to the fermentation broth to precipitate muconic acid, separating the muconic acid product from the fermentation broth and treating the fermentation broth with a basic reagent selected from metal hydroxides, oxides and carbonate compounds which causes the precipitation of a water-insoluble metal salt, and separating the metal salt precipitate to provide a resultant fermentation broth for recycle which contains a water-soluble ammonium compound.

The toluene component referred to above is a "non-growth" organic substrate. The microorganism does not metabolize the substrate for cell growth. Typical non-growth substrates include substituted and unsubstituted aromatic compounds such as benzene, xylene, ethylbenzene, phenol, catechol, naphthalene, and the like.

As noted in the Background Of The Invention section above, the microbiological oxidation of toluene to accumulated muconic acid requires the construction of mutant strains of microorganisms, e.g., as exemplified by *Pseudomonas putida* Biotype A strain ATCC 31,916.

This type of mutant strain can be provided by a process for microorganism construction which comprises (1) culturing microorganism species selectively to provide strain A1 which metabolizes toluene by the ortho pathway via catechol to muconic acid, and which subsequently metabolizes the resultant muconic acid via $\beta$-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

The starting microorganism can be any organism capable of growth on toluene and which possesses a catechol 1,2-oxygenase, e.g., a Pseudomonad. A variety of naturally occurring organisms have these traits including some members of the species *Pseudomonas putida, Pseudomonas aeruginosa, Pseudomonas fluorescens;* some members of the genera *Azotobacter* and *Nocardia;* and a number of unclassified fungi (both molds and yeasts).

The preferred constructed microorganisms are those described in copending patent application Ser. No. 287,344 (incorporated by reference), which possess a novel combination of enzymes which include (1) dihydrodihydroxybenzoate dehydrogenase enzyme; and (2) catechol 1,2-oxygenase enzyme with activity that is not inhibited in the presence of less than about five gram/liter of muconic acid in a growth medium.

Illustrative of suitable microorganisms are constructed strains of fluorescent Pseudomonads each of which has the following characteristics:

(a) possesses catechol 1,2-oxygenase enzyme with activity that is not inhibited in the presence of a low level of muconic acid in a growth medium;

(b) lacks substantially catechol 2,3-oxygenase enzyme;

(c) lacks functional muconate lactonizing enzyme;

(d) cells are rod shaped, vigorously motile and polarly flagellated; and (e) cells grow well on p-hydroxybenzoate.

Employing one of the constructed microorganisms described above for the production of muconic acid from toluene, the rate of toluene conversion typically is about 0.3–1.2 grams of muconic acid produced per dry weight gram of cells per hour. The conversion of toluene proceeds readily at a dry weight cell concentration of 1-3 grams per liter, with a resultant muconic acid production rate of 0.4-2 grams per liter per hour.

Under optimal conditions, the muconic acid accumulation limit can approach up to about 50 grams of muconic acid per liter of growth medium. The microbiological oxidation step of the present invention process normally is conducted at ambient temperatures up to about 31° C. The muconic acid at a concentration between about 10–45 grams/liter in the cell-free ammonia-neutralized aqueous fermentation medium is precipitated with sulfuric acid or phosphoric acid. The precipitated muconic acid (solubility at pH of 1-2, about 0.07% at 20° C.) is filtered, washed and dried. In a further embodiment of the present invention, the muconic acid is admixed with a solvent medium such as acetic acid (e.g., to form a 40 weight percent muconic acid/acetic acid slurry solution), and then treated under hydrogenation conditions to yield adipic acid.

The acidic filtrate (pH of 1-2) is neutralized with a basic reagent (e.g., calcium carbonate) to yield a precipitated salt (e.g., calcium sulfate with a solubility of 0.2 weight percent at 20° C.). The salt is recovered as a byproduct of the overall process.

The resultant fermentation broth is sterilized and recycled to the bioreactor. The bioconversion system can be operated in a continuous mode, without the continuous production of a waste byproduct stream.

The following examples are further illustrative of the present invention. The components and specific ingredients are pesented as being typical, and various modifications can be derived in view of the foregoing disclosure within the scope of the invention.

Carbon sources such as glucose, succinate, acetate or toluene are added aseptically prior to inoculation. Incubation conditions are in 250 ml shake flasks. Shaking is in a rotary shaker with temperature controlled at 28° C.

Growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophotometer.

Cultures are stored under liquid nitrogen.

EXAMPLE I

This Example illustrates the construction of a strain of microorganism which oxidizes toluene via the ortho ($\beta$-ketoadipate) pathway.

A series of mutants which metabolize toluene through the ortho pathway is constructed by first blocking the meta pathway and then isolating phenotypic revertants which have reacquired the ability to grow on benzoate. Strains prossessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31,916 type of mutant strain.

Strain MW 1210 of Example I is subjected to continuous cultivation with toluene as the sole source of carbon. Initially a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5 mm p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

EXAMPLE III

This Example illustrates the feasibility of the present invention process for separation of a carboxylic acid bioconversion-product from an aqueous fermentation medium, and for recovery of a resultant fermentation broth which is suitable for recycle.

A. Prior Art Method

To 500 ml of regular "NO" medium (Table I) are added 15 grams of cis, cis-muconic acid. The pH of the solution is about 4.18. A 14.4 ml quantity of 10N NaOH solution is added to adjust the pH to 6.2.

To the neutralized solution is added a 16 ml quantity of concentrated $H_2SO_4$ (18 M) solution, which lowers the pH of the solution to 0.98. White solids precipitate from the solution, and the solids are filtered, washed and recovered as muconic acid.

The acidic filtrate (500 ml) is neutralized to pH 6.2 with 10N NaOH and results in a soluble $Na_2SO_4$ solution in regular "NO" medium.

B. Invention Method

To 500 ml of regular "NO" medium are added 15 grams of cis, cis-muconic acid. The pH of the solution is about 4 12. A 14.2 ml quantity of concentrated $NH_4OH$ solution (15N) is added to adjust the pH to 6.2.

To the neutralized solution is added a 17 ml quantity of concentrated $H_2SO_4$ solution, which lowers the pH of the solution to 0.99. White solids precipitate from the solution, and the solids are filtered, washed and recovered as muconic acid (quantitative recovery; solubility of muconic acid at pH 1.0 is 0.03 wt %).

The acidic filtrate is neutralized to pH 6.6 with 13.3 g CaCO (lime), and results in a slurry solution containing precipitated white solids. The white solids ($CaSO_4$, solubility 0.2% in $H_2O$ at 20° C.) are filtered, washed and recovered (dry wt, 19.6 g).

The resultant fermentation broth filtrate contains dissolved $(NH_4)_2CO_3$, and the fermentation broth is suitable for recycle.

TABLE I

| MEDIUM COMPOSITIONS | | |
|---|---|---|
| Chemicals | (g/l) | (mM) |
| A. Regular "NO" Medium | | |
| $Na_2HPO_4$ | 7.1 | 50 |
| $KH_2PO_4$ | 13.6 | 100 |
| $(NH_4)_2SO_4$ | 2.25 | 17 |
| $MgSO_4.7H_2O$ | 0.246 | 1 |
| $CaCl_2$ | 0.0111 | 0.1 |
| $FeSO_4.7H_2O$ | 0.00278 | 0.01 |
| With appropriate growth carbon source in deionized water. | | |
| B. Modified "NO" Medium | | |
| $Na_2HPO_4$ | 7.1 | 50 |
| $KH_2PO_4$ | 13.6 | 100 |
| $(NH_4)_2SO_4$ | 0.281 | 2.1 |
| $MgSO_4.7H_2O$ | 0.738 | 3 |
| $CaCl_2$ | 0.0222 | 0.2 |
| $FeSO_4.7H_2O$ | 0.00834 | 0.03 |
| With appropriate growth carbon source in deionized water. | | |
| C. LP-1 Medium | | |
| $Na_2HPO_4$ | 1.42 | 10.0 |
| $KH_2PO_4$ | 2.72 | 20.0 |
| $(NH_4)_2SO_4$ | 0.749 | 5.67 |
| $MgSO_4.7H_2O$ | 0.738 | 3.0 |
| $CaCl_2$ | 0.0222 | 0.2 |
| $FeSO_4.7H_2O$ | 0.00834 | 0.03 |
| With appropriate growth carbon source in deionized water. | | |

EXAMPLE IV

This Example illustrates the present invention process as a continuous fermentation system with cell recycle and fermentation broth recycle for the production of muconic acid from toluene.

A. Inoculum Preparation

A *Pseudomonas putida* Biotype A strain ATCC No. 31,916 type of mutant strain culture (regular "NO" medium aqueous culture in polypropylene vial stored in liquid nitrogen) is thawed and transferred (1–1.5 ml) to a 250 ml shake flask containing 50 ml of regular "NO" medium (Table I) with 5 mM sodium succinate as the growth carbon source, and is incubated at 30° C. (250 RPM) for nine hours to an optical density of 50–60 klett units.

The 50 ml culture is transferred to a 2.5 liter shake flask containing one liter of LP-1 medium (Table I) with 20 mM sodium acetate as the carbon source and three polypropylene vials each with one ml toluene as the inducer, and is incubated at 30° C. (250 RPM) for 15 hours to an optical density of 60–90 klett units. The one liter culture is then inoculated into a 16 liter steam sterilizable fermentor (New Brunswick Scientific, Model SF 116) containing 11.5 liters of LP-1 medium with 20 mM of sodium acetate to start fermentation.

B. Enzyme Induction

After the inoculation toluene is supplied to the fermentor medium in vapor phase via air-stripping at an air-toluene vapor rate of 125 cc/min. The fermentation temperature is controlled at 30° C., the pH at 6.0 with 10N. ammonium hydroxide and 6N sulfuric acid solution, and a dissolved oxygen level at 30–100% saturation with 500 to 600 RPM agitation and 5 l/min aeration (approximately 0.5 VVM). Pluronic L61 polyol (BASF) is used as an antifoam agent.

As the optical density of the fermentation medium reaches 60–90 klett units (about 6–9 hours after inoculation), an aqueous solution containing 10 wt % acetic acid, 0.245 wt % $KH_2PO_4$ and 0.128 wt % $Na_2HPO_4$ is added to the fermentor medium at a rate of 0.4 ml/min. The air-toluene vapor rate is increased to 250 cc/min and then increased to 500 cc/min as the optical density reaches 250 klett units. The fed batch mode of fermentation is continued for 21 hours and the muconic acid product concentration reaches 12.6 g/l at a cell concentration of 2.1 g/l. The fermentation is then converted to a continuous operation with a cell recycle mode of operation.

C. Continuous/Cell Recycle

Starting the continuous/cell recycle operation, fresh membrane-sterilized LP-1 medium with 1.04 g/l acetic acid, 0.0256 g/l KH$_2$PO$_4$ and 0.0134 g/l Na$_2$HPO$_4$ concentration is pumped (FMI piston pump) into the fermentor at a rate of 38.3 ml/min. The fermentation broth is pumped from the fermentor with an internal circulation pump (Micro gear pump) to a romicon ® hollow tube ultrafilter with a polysulfone type ultrafiltration membrane (PM-100; molecular weight cutoff of 100,000). Total membrane area is 1.1 ft$^2$ (50 tubes in a 1.0"×25" cylindrical polypropylene cartridge).

The fermentation broth with cells is "cross-flow" filtered by the ultrafilter controlled at a permeate (clean, cell-free product stream) rate of 36 to 39 ml/min. The fermentation broth with cells is continuously circulated "through" the ultrafilter at an internal circulation rate of 4.5 l/min and a pressure drop of five to ten psig across the ultrafiltration membrane. Three hours after starting the continuous/cell recycle operation without purge, the cell concentration reaches 2.8 g/l. A purge stream at a rate of 2.7 ml/min is then maintained during the continuous/cell recycle run. After initial decrease, the product concentration in the cell-free permeate stream is maintained at 6.8 to 7.0 g/l at a permeate rate of 38 ml/min. The air-toluene vapor rate is increased to 1000 ml/min.

During this type of steady state continuous/cell recycle mode of operation, a reactor productivity of 1.4 g muconic acid/l/hr (0.20 hr$^{-1}$×6.9 g/l) is achieved and a specific productivity of 0.58 g muconic acid/g cells/hr (6.9 g/l×0.2 hr$^{-1}$/2.4 g/l) is maintained.

D. Product Recovery And Fermentation Broth Recycle

The continuous operation is modified to include a product recovery procedure and a recycle of fermentation broth.

In the manner of Example IIIB, a solution of concentrated H$_3$PO$_4$ is added to the cell-free permeate to precipitate the muconic acid product. The precipitate is separated by filtration.

The acidic filtrate is neutralized with BaCO$_3$ which results in the formation and precipitation of BaHPO$_4$ solids. The solids are separated by filtration.

The resultant fermentation broth filtrate, which contains (NH$_4$)$_2$CO$_3$ solute, is emulsified with toluene and air sterilized, and then recycled to the fermentor. The quantity of NH$_4$OH fed to the fermentor is reduced by an amount corresponding to the molar input of (NH$_4$)$_2$CO$_3$ contained in the recycled fermentation broth.

E. Adipic Acid Production

Muconic acid is dissolved in acetic acid to form a 40% muconic acid/acetic acid slurry solution.

The slurry solution is fed to a hydrogenation fixed-bed reactor (at 102° C. and 3 atm) with Pd/C as the catalyst.

The hydrogenation product solution is flashed and distilled to separate acetic acid. The heavy end slurry, which consists substantially of adipic acid, is washed to remove trace acetic acid, and dried.

What is claimed is:

1. In a microbial bioconversion process in which a non-growth organic substrate in an aqueous fermentation medium is bio-oxidized by whole cells to an extracellular carboyxlic acid product having a solubility of less than about 1.0 weight percent in the aqueous fermentation medium, the improvement which comprises neutralizing the acidic pH conditions in the fermentation medium by the addition of ammonia during the bioconversion period, separating the microbial cells from the fermentation medium to provide a cell-free fermentation broth containing ammonium carboxylate product, adding sulfuric acid or phosphoric acid to the fermentation broth to precipitate the carboxylate product in the free carboxylic acid form, separating the carboxylic acid precipitate from the fermentation broth and treating the fermentation broth with a basic reagent selected from the group consisting of metal hydroxides, oxides and carbonate compounds which causes the precipitation of a water-insoluble metal salt, and separating the metal salt precipitate to provide a resultant fermentation broth for recycle which contains a water-soluble ammonium compound.

2. A bioconversion process in accordance with claim 1 wherein the non-growth substrate is an aromatic hydrocarbon.

3. A bioconversion process in accordance with claim 1 wherein the carboxylic acid product is a dicarboxylic acid.

4. A bioconversion process in accordance with claim 1 wherein the basic reagent is a magnesium compound.

5. A bioconversion process in accordance with claim 1 wherein the basic reagent is a calcium compound.

6. A bioconversion process in accordance with claim 1 wherein the basic reagent is a zinc compound.

7. A bioconversion process in accordance with claim 1 wherein the basic reagent is a barium compound.

8. In a microbial bioconversion process in which a toluene substrate in an aqueous fermentation medium is bio-oxidized by whole cells to an extracellular muconic acid product, the improvement which comprises neutralizing the acidic pH conditions in the fermentation medium by the addition of momonia during the bioconversion period, separating the microbial cells from the fermentation medium to provide a cell-free fermentation broth containing ammonium muconate product, adding sulfuric acid or phosphor acid to the fermentation broth to precipitate muconic acid, separating the muconic acid product from the fermentation both and treating the fermentation broth with a basic reagent selected from the group consisting of metal hydroxides, oxides and carbonate compounds which causes the precipitation of a water-insoluble metal salt, and separating the metal salt precipitate to provide a resultant fermentation broth for recycle which contains a water-soluble ammonium compound.

9. A process in accordance with claim 8 wherein the basic reagent is a calcium compound.

10. A process in accordance with claim 8 wherein the basic reagent is calcium carbonate.

11. A process in accordance with claim 8 wherein the bioconversion is conducted continuously, and the recovered cell-free fermentation broth is recycled continuously.

12. A process in accordance with claim 8 wherein the bioconversion is accomplished by a microorganism strain which possesses catechol 1,2-oxygenase enzyme with activity that is not inhibited in the presence of a low level of muconic acid in the aqueous fermentation medium.

13. A process in accordance with claim 8 wherein the bioconversion is accomplished by *Pseudomonas putida* Biotype A strain ATCC 31,916.

14. A process in accordance with claim 8 wherein the bioconversion is accomplished by a fluorescent Pseudomonas microorganism having the following characteristics:

(a) possesses catechol 1,2-oxygenase enzyme with activity that is not inhibited in the presence of a low level of muconic acid in a growth medium;
(b) lacks substantially catechol 2,3-oxygenate enzyme;
(c) lacks functional muconate lactonizing enzyme;
(d) cells are rod shaped, vigorously motile and polarly flagellated; and
(e) cells grow well on p-hydroxybenzoate.

* * * * *